(12) United States Patent
Druzkowski et al.

(10) Patent No.: US 6,683,203 B2
(45) Date of Patent: Jan. 27, 2004

(54) PROCESS FOR THE MANUFACTURE OF AQUEOUS SOLUTIONS OF UNSATURATED QUATERNARY AMMONIUM SALTS

(75) Inventors: Thierry Druzkowski, Paris (FR); Gilles Herbst, Nancy (FR); Serge Tretjak, Roulhing (FR); Alain Riondel, Forbach (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 10/132,690

(22) Filed: Apr. 26, 2002

(65) Prior Publication Data

US 2003/0023113 A1 Jan. 30, 2003

(30) Foreign Application Priority Data

Apr. 26, 2001 (FR) .............................. 01 05701

(51) Int. Cl.[7] .............................................. C07C 69/52
(52) U.S. Cl. ...................................................... 560/222
(58) Field of Search ........................................ 560/222

(56) References Cited

U.S. PATENT DOCUMENTS

| | | |
|---|---|---|
| 5,912,383 A | 6/1999 | Riondel et al. |
| 6,171,505 B1 * | 1/2001 | Maury et al. ............... 210/727 |

FOREIGN PATENT DOCUMENTS

| | | |
|---|---|---|
| DE | 3048 020 A1 | 7/1982 |
| EP | 0 250 325 A2 | 12/1987 |
| EP | 0281 718 A2 | 9/1988 |
| EP | 0 329 512 A | 8/1989 |
| EP | 0420790 A1 | 4/1991 |
| EP | 0 428 970 A | 5/1991 |
| EP | 0663386 A1 | 7/1995 |
| EP | 0930 290 A1 | 7/1999 |
| FR | 1 529 000 A | 10/1968 |
| FR | 2 027 225 | 9/1970 |
| FR | 2 707 291 | 1/1995 |
| FR | 2 788 767 | 7/2000 |
| WO | WO 89/07588 | 8/1989 |

OTHER PUBLICATIONS

Perry's Chemical Engineers' Handbook 6th ed, McGraw–Hill Book Co., p. "21–77" (1984).*
Abstract of JP 07 238057 A, Sep. 12, 1995.
Abstract of JP 10 072433 A, Mar. 17, 1998.

* cited by examiner

*Primary Examiner*—Richard L. Raymond
*Assistant Examiner*—Zachary C. Tucker
(74) *Attorney, Agent, or Firm*—Millen, White, Zelano & Branigan, P.C.

(57) ABSTRACT

This process for the manufacture of an aqueous solution of the unsaturated quaternary ammonium salt corresponding to the formula (I), by reaction, in the presence of water, of N,N-dimethylaminoethyl acrylate (DAMEA) with a quaternizing agent of formula (II), is characterized in that the said reaction is carried out continuously in a rotating disc agitated column, with introduction of the quaternizing agent in the column bottom and introduction of the DAMEA and the water in the column top, the said reaction being carried out at a temperature of 35 to 60° C. and under a pressure of 10 to 20 bar.

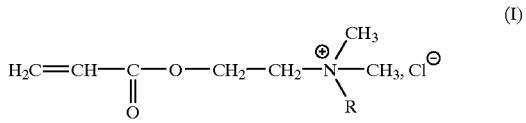

(I)

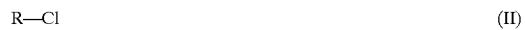

(II)

R=methyl or benzyl radical.

15 Claims, 1 Drawing Sheet

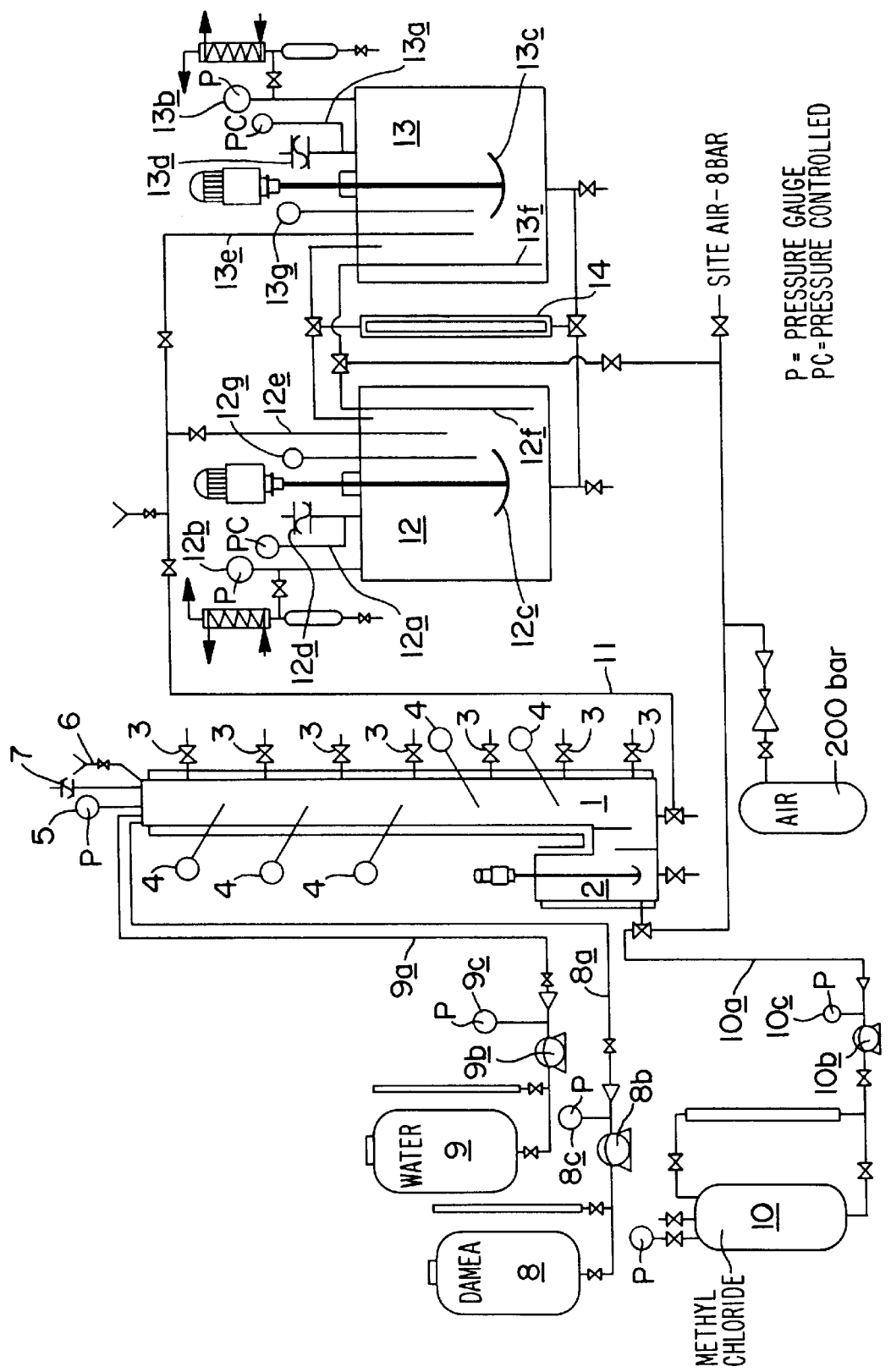

PROCESS FOR THE MANUFACTURE OF AQUEOUS SOLUTIONS OF UNSATURATED QUATERNARY AMMONIUM SALTS

CROSS-REFERENCE TO RELATED APPLICATIONS

The present application is related to U.S. Application No. 10/132,739, filed Apr. 26, 2002 based on French priority application No. 01.05609 filed Apr. 26, 2001 and U.S. Application No. 10/132,691, filed Apr. 26, 2002 based on French priority application No. 01.05610, filed Apr. 26, 2001.

The present invention relates to the manufacture of aqueous solutions of unsaturated quaternary ammonium salts (hereinafter denoted quaternary salts) corresponding to the following formula (I):

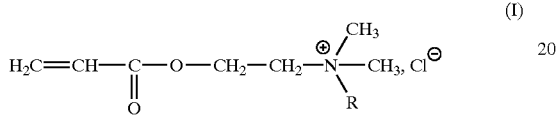

in which R represents methyl or benzyl, by reaction, in the presence of water, of N,N-dimethyl-aminoethyl acrylate (DAMEA) with a quaternizing agent of formula (II):

in which R is as defined above.

Aqueous solutions of quaternary salts (I) are used to prepare polymers intended to act as cationic flocculents in water treatment.

European Patent EP-B-250 325 discloses a process for the preparation of aqueous solutions of quaternary salts, including those of formula (I), according to which process, in the presence of at least one polymerization inhibitor:

in a first stage (a), DAMEA is reacted with 5 to 20% by weight of the amount by weight of the quaternizing agent necessary for the reaction or, according to an alternative form (a'), with 5 to 20% by weight, with respect to the weight of the DAMEA, of an aqueous solution of quaternary salts, which solution comprises from 50 to 85% by weight of quaternary salts; and in a second stage (b), the water and the quaternizing agent are continuously added until the desired concentration of quaternary salts in the water is obtained.

During stages (a) and (b), the temperature is maintained at a value of between 30 and 60° C. Furthermore, during stages (a) and (b) and in particular near the end of the reaction, a stream of oxygenated gas is maintained in the reaction medium such that the ratio by volume (or volumetric throughput) of total gas at the outlet of the reactor to the volume (or volumetric throughput) of oxygen introduced at the inlet of this same reactor is less than 100.

This process makes it possible to prepare aqueous solutions of quaternary salts which have a stability at ambient temperature of greater than one year. However, a particularly high content of impurities, in particular of

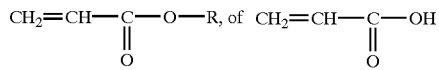

and of DAMEA, is found in these solutions. In addition, this process requires relatively long reaction times, which represents an obvious economic disadvantage.

A process intended to reduce the formation of the impurities during the quaternization reaction was then provided in International Application WO 89/07 588. In accordance with this process, the reaction is carried out at a temperature of between 10 and 80° C., and in a first stage, all or a portion of the quaternizing agent necessary for the reaction is introduced into the reactor, this agent being in the liquid state under the reaction conditions, subsequently, the DAMEA is added, and as soon as 0 to 30% of the stoichiometry of the DAMEA has been introduced into the reactor, the remainder of the quaternizing agent, the remainder of the DAMEA and the water are continuously and simultaneously added until the desired concentration of quaternary salts is obtained, and, in the case where the quaternizing agent is introduced in the gaseous state at the reaction temperature, the reaction is carried out in the presence of oxygen and a pressure is applied so that the quaternizing agent is liquid at the reaction temperature and, at the end of the reaction, the pressure is gradually decreased to atmospheric pressure and, simultaneously, a ratio as volumetric throughput of total gas at the outlet of the reactor to the volumetric throughput of oxygen introduced into the reactor of less than 100 is imposed.

The above process according to WO 89/07 588 introduces significant improvements to the process according to EP-B-250 325. However, it transpired that the purity with which the quaternary salts are obtained is still insufficient. Thus, during the reaction of DAMEA with $CH_3Cl$ in an aqueous medium, resulting in the salt also denoted subsequently by the abbreviation ADAMQUAT MC, the dimer of ADAMQUAT MC, represented by the formula (1):

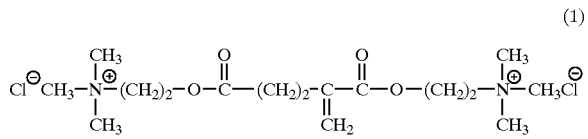

is formed as impurity, in addition to acrylic acid (AA), formed by hydrolysis of DAMEA.

By virtue of a series of tests of reactivity with respect to polymerization, it was possible to demonstrate that these impurities affected the quality of the cationic polymers derived from the ADAMQUAT.

Thus, operating conditions for the preparation of aqueous solutions of the salt of formula (I) which are capable of minimizing the abovementioned impurities, so as to provide a salt (I) in aqueous solution of very high analytical quality have been sought.

This novel process, which thus forms the subject-matter of the present invention and which exhibits the important additional advantage of providing a product of consistent quality, is characterized in that the said reaction is carried out continuously in a rotating disc agitated column, with introduction of the quaternizing agent at the column bottom and introduction of the DAMEA and the water at the column top, the said reaction being carried out at a temperature of 35 to 60° C., preferably at a temperature of 40 to 50° C., and under a pressure of 10 to 20 bar, preferably of 12 to 16 bar.

Preferably, the reaction is carried out at 35–60° C. because there is a tendency for polymerization to occur at temperatures above 60° C., although this tendency can be overcome by altering conditions, such as adding a polymerization inhibitor or altering stoichiometric ratios. Likewise, there is a tendency for no reaction to occur below 35° C., although this tendency can be overcome by altering conditions, such as adding a catalyst.

Furthermore, the reaction is generally carried out with a molar ratio of $CH_3Cl$ to the DAMEA which is between 1 and 1.5, in particular between 1.02 and 1.15, and a residence time of 2 to 6 hours, in particular of 2.5 to 3.5 hours. With respect to the ratio of the throughput for the introduction of water/throughput for the introduction of quaternizing agent, it is generally between 0.3 and 1.2, in particular between 0.5 and 0.9.

Furthermore, the process according to the present invention is advantageously carried out in the presence of at least one stabilizer chosen in particular from 3,5-di(tert-butyl)-4-hydroxytoluene, hydroquinone methyl ether, hydroquinone, catechol, tert-butylcatechol and the mixtures of these stabilizers, the content of stabilizing agent(s) being in particular from 20 to 2000 ppm, preferably from 100 to 1200 ppm, with respect to the aqueous solution of quaternary salt (I).

In addition, the process according to the invention is advantageously carried out in the presence of at least one sequestering agent for metals chosen in particular from diethylenetriaminepentaacetic acid, the pentasodium salt of diethylenetriaminepentaacetic acid, N-(hydroxyethyl) ethylene-diaminetriacetic acid and the trisodium salt of N-(hydroxyethyl)ethylenediaminetriacetic acid, the content of sequestering agent(s) being in particular from 1 to 100 ppm, preferably from 5 to 30 ppm, with respect to the aqueous solution of quaternary salt (I).

Generally, the sequestering agents are added in the form of an aqueous solution, as they are generally available in this form. Thus, the pentasodium salt of diethylenetriaminepentaacetic acid sold under the name Versenex 80 is provided in the form of an approximately 40% by weight aqueous solution.

The process according to the invention makes it possible in particular to prepare aqueous solutions having a concentration of quaternary salts (I) of 50 to 85% by weight and comprising very low amounts of impurities, as illustrated in Table 1 below.

The following examples illustrate the present invention without, however, limiting the scope thereof. In these examples, the percentages are by weight, unless otherwise indicated.

BRIEF DESCRIPTION OF THE DRAWING

The single FIGURE of the appended drawing represents the plant used for the continuous manufacture of the aqueous solutions of acryloyloxyethyltrimethylammonium chloride according to the examples. This plant is described in Example 1.

EXAMPLE 1

Continuous Manufacture of an Aqueous Solution of ADAMQUAT MC

Use is made of a rotating disc agitated column (1) composed of a stainless steel tube with a capacity of 0.5 liter which comprises a zone (2) for premixing the reactants (1/10 of the total volume) and which is equipped with seven sampling points (3), with five temperature recorders (4), with a pressure gauge (5), with a corner valve tared at 17 bar (6), with a bursting disc tared at 25 bar (7) and with branch pipes which make possible the introduction of the reactants.

Each of the three feed tanks (8; 9; 10), for DAMEA, water and methyl chloride respectively, is connected to the agitated column (1) via a feed pipe (respectively 8a; 9a; 10a) with the interposition of a feed pump (8b; 9b; 10b) and of a pressure gauge (respectively 8c; 9c; 10c). The pipe (10a) for feeding with methyl chloride emerges in the column bottom and the two DAMEA and water feed pipes (respectively 8a; 9a) emerge in the column top.

When operating, the ADAMQUAT MC, in aqueous solution, the density of which is greater than that of the DAMEA and than that of the methyl chloride, exits via the bottom of the column (1) and is diverted via an outlet pipe (11) into one of the two tanks (12; 13), each equipped with a pressure regulator (12a; 13a), with a pressure gauge (12b; 13b), with a specific stirrer (12c; 13c) operating under pressure, with a bursting valve tared at 25 bar (12d; 13d), with a degasser (12e; 13e), with an air introduction point (12f; 13f), with a level indicator (14) and with temperature recorders (12g; 13g). The tank into which the ADAMQUAT MC in aqueous solution is directed is used as degasser. Once filled, it is isolated and its contents are degassed and then discharged, the ADAMQUAT MC in aqueous solution exiting from the column (1) then being directed into the other tank, where it will be degassed and then discharged. In other words, the column operates continuously and, for the degassing operation, the installation operates semicontinuously.

The procedure is as follows:

550 g of finished ADAMQUAT MC 80 (80% aqueous solution) are charged to the column (1). The installation is placed under pressure (11 bar) using a depleted air cylinder at 200 bar. Once the column (1) has been brought to the desired working temperature of 45° C., the three feed pumps (8b; 9b; 10b) are started up and their throughputs are adjusted according to the mean residence time of 2.93 hours and the targeted $CH_3Cl$/DAMEA molar ratio of 1.18. To this end, the throughput for introduction of the DAMEA is 120 ml/h, that of the water is 35 ml/h and that of the methyl chloride is between 49 and 53 ml/h. Under these conditions, the $CH_3Cl$/DAMEA molar ratio lies between 1.14 and 1.23 (mean molar ratio: 1.18) and the ratio of the throughput for feeding with water/throughput for feeding with $CH_3Cl$ lies between 0.71 and 0.78, and the residence time is 2.93 hours.

The results are given in the following Table 1. The degree of conversion of the DAMEA remained at 100% and the steady-state conditions were achieved after operating for 7.5 hours.

The analytical techniques were as follows:

the percentage of ADAMQUAT MC was determined by potentiometry, making it possible to quantitatively determine the chloride ions by means of silver nitrate.

the impurities AA and ADAMQUAT MC dimer were analysed by high performance liquid chromatography (HPLC).

EXAMPLE 2

The preparation was carried out as in Example 1, except that the $CH_3Cl$/DAMEA molar ratio was reduced. The operating conditions and the results are also listed in Table 1. The degree of conversion of the DAMEA remained at 100% for an operating time of 6 hours.

The preceding examples can be repeated with similar success by substituting the generically or specifically described reactants and/or operating conditions of this invention for those used in the preceding examples.

The entire disclosures of all applications, patents and publications, cited herein and of corresponding French application No. 01.05701, filed Apr. 27, 2001 is hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

TABLE 1

| Example | Temperature (°C.) | Pressure (bar) | Throughput of the reactants (ml/h) DAMEA | Water | CH₃Cl | Residence time (h) | Mean CH₃Cl/DAMEA molar ratio | Ratio of the throughput for feeding with water/throughput for feeding with CH₃Cl | Duration (min) | ADAMQUAT MC (%) | Water (%) | AA* (ppm) | ADAMQUAT MC** dimer (ppm) |
|---|---|---|---|---|---|---|---|---|---|---|---|---|---|
| 1 | 45 | 11 | 120 | 35 | 49–53 | 2.93 | 1.18 | 0.71–0.78 | charge | 78.4 | 20.4 | 2001 | 1456 |
| | | | | | | | | | 105 | 81 | 27.1 | 1552 | 1515 |
| | | | | | | | | | 195 | 72.8 | 27.1 | 820 | 328 |
| | | | | | | | | | 315 | 76.3 | 22.5 | 531 | 141 |
| | | | | | | | | | 450 | 80.5 | 18.2 | 329 | / |
| | | | | | | | | | 585 | 82.9 | 17.6 | 237 | / |
| | | | | | | | | | 635 | 82.8 | 20.4 | 288 | / |
| 2 | 45 | 11 | 120 | 35 | 44–47 | 3 | 1.05 | 0.81–0.86 | charge | 81.3 | 19.7 | 1221 | 1309 |
| | | | | | | | | | 120 | 74.2 | 26.2 | 1100 | 1181 |
| | | | | | | | | | 180 | 77 | 23.9 | 669 | 408 |
| | | | | | | | | | 370 | 80.4 | 20.3 | 360 | 149 |
| | | | | | | | | | 555 | 80.4 | 19.8 | 214 | / |

*AA = Acrylic acid;
**ADAMQUAT MC = Acryloyloxyethyltrimethylammonium chloride

What is claimed is:

1. A process for preparing an aqueous solution of an unsaturated quaternary ammonium salt of the following formula (I):

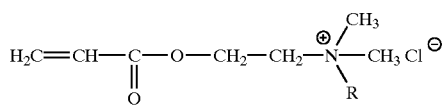

in which R represents a methyl or benzyl radical,
by reaction, in the presence of water, of N,N-dimethylaminoethyl acrylate (DAMEA) with a quaternizing agent of formula (II):

R—Cl  (II)

in which R is as defined above,
wherein the reaction is carried out continuously in a rotating disk agitated column, with introduction of the quaternizing agent in the column bottom and introduction of the DAMEA and the water in the column top, the reaction being carried out at a temperature of 35–60° C. and under a pressure of 10–20 bar.

2. A process according to claim 1, wherein the reaction is carried out at a temperature of 40–50° C.

3. A process according to claim 1, wherein the reaction is carried out under a pressure of 12–16 bar.

4. A process according to claim 1, wherein the reaction is carried out with a molar ratio of CH₃Cl to the DAMEA of 1–1.5.

5. A process according to claim 4, wherein the reaction is carried out with a molar ratio of the quaternizing agent to the DAMEA of 1.02:1–1.15:1.

6. A process according to claim 1, wherein the reaction is carried out with a ratio of the throughput for the introduction of water/throughput for the introduction of quaternizing agent of 0.3:1–1.2:1.

7. A process according to claim 1, wherein the reaction is carried out with a residence time of 2–6 hours.

8. A process according to claim 1, wherein the reaction is carried out with a residence time of 2.5–3.5 hours.

9. A process according to claim 1 further comprising reacting in the presence of at least one stabilizer of 3,5-di(tert-butyl)-4-hydroxytoluene, hydroquinone methyl ether, hydroquinone, catechol, tert-butylcatechol or a mixture thereof, the content of stabilizing agent(s) being from 20–2000 ppm, with respect to the aqueous solution of quaternary salt (I).

10. A process according to claim 9, further comprising reacting in the presence of at least one sequestering agent for metals of diethylenetriaminepentaacetic acid, the pentasodium salt of diethylenetriaminepentaacetic acid, N-(hydroxyethyl)ethylene-diaminetriacetic acid, or the trisodium salt of N-(hydroxyethyl)ethylene-diaminetriacetic acid, the content of sequestering agent(s) being 1–100 ppm, with respect to the aqueous solution of quaternary salt (I).

11. A process according to claim 1, wherein the reaction is carried out with a ratio of the throughput for the introduction of water/throughput for the introduction of quaternizing agent of 0.5:1–0.9:1.

12. A process according to claim 1 further comprising conducting in the presence of at least one stabilizer of 3,5-di(tert-butyl)-4-hydroxytoluene, hydroquinone methyl ether, hydroquinone, catechol, tert-butylcatechol or a mixture thereof, the content of stabilizing agent(s) being from 100–1200 ppm, with respect to the aqueous solution of quaternary salt (I).

13. A process according to claim 9, further comprising reacting in the presence of at least one sequestering agent for metals of diethylenetriaminepentaacetic acid, the pentasodium salt of diethylenetriaminepentaacetic acid, N-(hydroxyethyl)ethylene-diaminetriacetic acid, or the trisodium salt of n-(hydroxyethyl)ethylene-diaminetriacetic acid, the content of sequestering agent(s) being 5–30 ppm, with respect to the aqueous solution of quaternary salt (I).

14. A process according to claim 1, further comprising diverting the unsaturated quaternary ammonium salt of formula (I) into a tank, introducing air, and degassing.

15. A process according to claim 14, further comprising discharging the degassed contents of the tank into a second tank, introducing air, and degassing.

* * * * *

UNITED STATES PATENT AND TRADEMARK OFFICE
CERTIFICATE OF CORRECTION

PATENT NO. : 6,683,203 B2
DATED : January 27, 2004
INVENTOR(S) : Thierry Druzkowski It is certified that error appears in the above-identified patent and that said Letters Patent is hereby corrected as shown below:

Title page,
Item [30], Foreign Application Priority Data, reads "April 26, 2001" should read -- April 27, 2001 --

Column 6,
Line 67, reads "n-(hydroxyethyl)" should read -- N-(hydroxyethyl) --

Signed and Sealed this

Twelfth Day of April, 2005

JON W. DUDAS
*Director of the United States Patent and Trademark Office*